(12) United States Patent
Wotton, III (10) Patent No.: US 8,177,818 B2
(45) Date of Patent: May 15, 2012

(54) FIXATION PLATE

(75) Inventor: Harold M. Wotton, III, Woodstock, CT (US)

(73) Assignee: Securos, Inc., Charlton, MA (US)

( * ) Notice: Subject to any disclaimer, the term of this patent is extended or adjusted under 35 U.S.C. 154(b) by 744 days.

(21) Appl. No.: 11/221,471

(22) Filed: Sep. 8, 2005

(65) Prior Publication Data

US 2006/0212035 A1    Sep. 21, 2006

(51) Int. Cl.
*A61B 17/80* (2006.01)
(52) U.S. Cl. .................................................. 606/280
(58) Field of Classification Search .................. 606/53, 606/280–299, 70, 71, 913; D24/155
See application file for complete search history.

(56) References Cited

U.S. PATENT DOCUMENTS

| | | | |
|---|---|---|---|
| 4,461,092 A * | 7/1984 | Hore | 33/474 |
| 4,565,193 A * | 1/1986 | Streli | 606/297 |
| 4,867,144 A | 9/1989 | Karas et al. | |
| 4,926,564 A * | 5/1990 | Loggins | 33/474 |
| 4,955,886 A * | 9/1990 | Pawluk | 606/280 |
| 4,988,350 A * | 1/1991 | Herzberg | 606/65 |
| 5,197,966 A | 3/1993 | Sommerkamp | |
| 5,304,180 A * | 4/1994 | Slocum | 606/282 |
| 5,785,713 A | 7/1998 | Jobe | |
| 5,864,959 A * | 2/1999 | Johansen et al. | 33/474 |
| 5,868,746 A | 2/1999 | Sarver | |
| 6,096,040 A * | 8/2000 | Esser | 606/280 |
| 6,190,390 B1 * | 2/2001 | McAllister | 606/87 |
| D443,060 S * | 5/2001 | Benirschke et al. | D24/155 |
| 6,358,250 B1 * | 3/2002 | Orbay | 606/86 B |
| D463,558 S * | 9/2002 | Bryant et al. | D24/155 |
| D469,533 S * | 1/2003 | Bryant et al. | D24/155 |
| D469,874 S * | 2/2003 | Bryant et al. | D24/155 |
| 6,623,486 B1 * | 9/2003 | Weaver et al. | 606/281 |
| D536,453 S * | 2/2007 | Young et al. | D24/155 |
| 2002/0147450 A1 * | 10/2002 | LeHuec et al. | 606/61 |
| 2002/0156474 A1 * | 10/2002 | Wack et al. | 606/69 |
| 2004/0030339 A1 * | 2/2004 | Wack et al. | 606/69 |
| 2004/0097936 A1 * | 5/2004 | Ebid | 606/69 |
| 2004/0127897 A1 * | 7/2004 | Freid et al. | 606/61 |

(Continued)

FOREIGN PATENT DOCUMENTS

DE      10320124 B3      9/2004

(Continued)

OTHER PUBLICATIONS

"Metallurgical Evaluation of the Slocum TPLO Plate", Boudrieau et al., paper presented at the 32$^{nd}$ Annual Conference of the Veterinary Orthopedic Society, p. 15, Mar. 5-12, 2005, available at <http://www.vosdvm.org> as shown by the attached cover sheet.

*Primary Examiner* — Eduardo C Robert
*Assistant Examiner* — Jerry Cumberledge
(74) *Attorney, Agent, or Firm* — Iandiorio Teska & Coleman, LLP (57) ABSTRACT

A fixation plate with a base section including apertures for fixation to one bone segment and a leg section extending from the base section and including apertures for fixation to another bone segment. The expanse of the base section tapers gradually to smoothly cojoin with the leg section and the expanse of the leg section continues to taper to a distal rounded end of the leg section.

9 Claims, 5 Drawing Sheets

U.S. PATENT DOCUMENTS

| | | | |
|---|---|---|---|
| 2004/0153073 A1* | 8/2004 | Orbay | 606/69 |
| 2004/0167522 A1* | 8/2004 | Niederberger et al. | 606/69 |
| 2004/0167530 A1* | 8/2004 | Hamel | 606/86 |
| 2004/0236334 A1* | 11/2004 | Michelson | 606/69 |
| 2005/0015089 A1* | 1/2005 | Young et al. | 606/69 |
| 2005/0021033 A1* | 1/2005 | Zeiler et al. | 606/70 |
| 2005/0065524 A1* | 3/2005 | Orbay | 606/69 |
| 2005/0124994 A1* | 6/2005 | Berger et al. | 606/61 |
| 2005/0182405 A1* | 8/2005 | Orbay et al. | 606/69 |
| 2005/0234458 A1* | 10/2005 | Huebner | 606/69 |
| 2005/0240185 A1* | 10/2005 | Boomer et al. | 606/69 |
| 2005/0240187 A1* | 10/2005 | Huebner et al. | 606/69 |
| 2006/0025776 A1 | 2/2006 | Thorsgard | |

FOREIGN PATENT DOCUMENTS

| | | | |
|---|---|---|---|
| GB | 2245498 | * | 1/1992 |
| JP | 2004223042 | * | 8/2004 |
| WO | WO 2005/053553 A1 | | 6/2005 |

* cited by examiner

FIXATION PLATE

FIELD OF THE INVENTION

This subject invention relates to a bone fixation plate.

BACKGROUND OF THE INVENTION

Bone fixation plates are used in tibial osteotomy and other procedures to secure two bone segments together. In a tibial osteotomy, for example, a curvilinear cut is made in the canine proximal tibia to separate the metaphysis from the proximal tibia. Next, the metaphysis is rotated to level the tibial plateau. Finally, the metaphysis is fixed to the proximal tibia by a fixation plate. See U.S. Pat. No. 5,304,180 incorporated herein by this reference. The fixation plate of this patent includes a broad triangular portion to be fixed to the metaphysis of the tibia and a narrower leg section to be fixed to diaphysis of the tibia. There are three bone screw holes in the triangular portion and three bone screw holes in the leg section.

The fixation plate produced in accordance with this patent, however, is cast from surgical grade stainless steel and thus is relatively thick (approximately 5 mm). Also, there have been reports of an increased tumor occurrences when these fixation plates are used. See "Metallurgical Evaluation of the Slocum TPLO Plate", Boudrieau et al., paper presented at the 32$^{nd}$ Annual Conference of the Veterinary Orthopedic Society, Mar. 5-12, 2005.

U.S. Pat. Nos. 4,867,144 and 4,988,350 disclose other configurations for bone fixation plates. In many fixation plates, there is a fairly sharp transition between the wide and narrow sections of the fixation plate resulting in a possible weak stress zone subject to breakage.

SUMMARY OF THE INVENTION

It is therefore an object of this invention to provide a different kind of bone fixation plate useful in tibial osteotomy and other procedures.

It is a further object of this invention to provide such a bone fixation plate which is thinner, lightweight, and strong.

It is a further object of this invention to provide such a bone fixation plate in which there is no sharp transition between the two sections of the fixation plate.

The subject invention results from the realization that a thinner, lighter weight, and stronger bone fixation plate with no sharp transitions is effected by a base section which tapers smoothly to co-join with a leg section which then continues to taper smoothly to a rounded distal end.

The subject invention, however, in other embodiments, need not achieve all these objectives and the claims hereof should not be limited to structures or methods capable of achieving these objectives.

This invention features, in one example, a fixation plate comprising a base section including apertures for fixation to one bone segment and a leg section extending from the base section and including apertures for fixation to another bone segment. The expanse of the base section tapers gradually to smoothly cojoin with the leg section.

Typically, the expanse of the leg section continues to taper to a distal rounded end of the leg section and the proximal end of the base section is angled. In one preferred embodiment, both sides of the plate are straight and one side smoothly diverges away from the other. Also, the plate is preferably anatomically pre-contoured such that the contour of the base section is different than the contour of the leg section. In one example, the contour of the base section is greater than the contour of the leg section and preferably the change in contour is smoothly progressive from the distal end of the leg section to the proximal end of the base section.

In one example, there are at least two spaced elongate apertures in the base section each having the same first long axis. There may also be a third spaced elongate aperture in the base section having a second long axis intersecting the first long axis at an angle of between 55 and 60°. Preferably, there are at least two spaced round apertures in the leg section and the centers of the two spaced round apertures are on the first long axis. There may be a third spaced round aperture in the leg section offset from the first long axis and located proximate the proximal end of the leg section. In the preferred embodiment, there are spaced elongate apertures in the base section each with one beveled end and beveled sides and spaced round beveled apertures in the leg section. Typically, the minimum spacing between any two apertures in the base section is greater than or equal to 0.2" and the minimum spacing between any two apertures in the leg section is greater than or equal to 0.2". A typical fixation plate in accordance with this invention has a maximum thickness of 0.275" and is made of machined implant grade (certified) stainless steel.

One fixation plate in accordance with the subject invention features a base section including apertures and a leg section extending from the base section. The sides of the plate are straight with one side smoothly diverging away from the other from a distal end of the leg section to a proximal end of the base section.

A fixation plate in accordance with this invention features a wider base section including at least two spaced elongate apertures each having the same first long axis and a narrower leg section extending from the base section. Typically, the expanse of the base section tapers gradually to smoothly cojoin with the leg section and the expanse of the leg section continues to taper to a distal rounded end of the leg section.

BRIEF DESCRIPTION OF THE DRAWINGS

Other objects, features and advantages will occur to those skilled in the art from the following description of a preferred embodiment and the accompanying drawings, in which.

DISCLOSURE OF THE PREFERRED EMBODIMENT

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1:
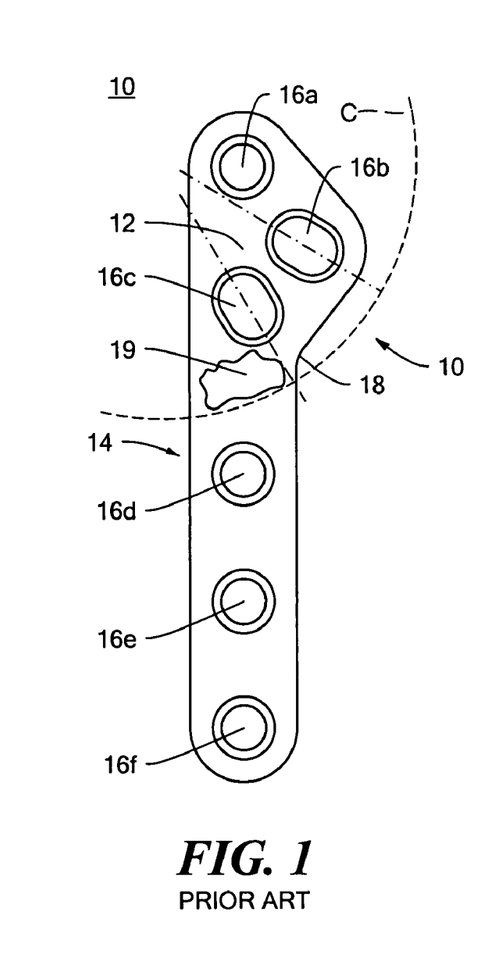
FIG. 1 is a schematic front view of a bone fixation plate in accordance with the prior art.
Figure 2:
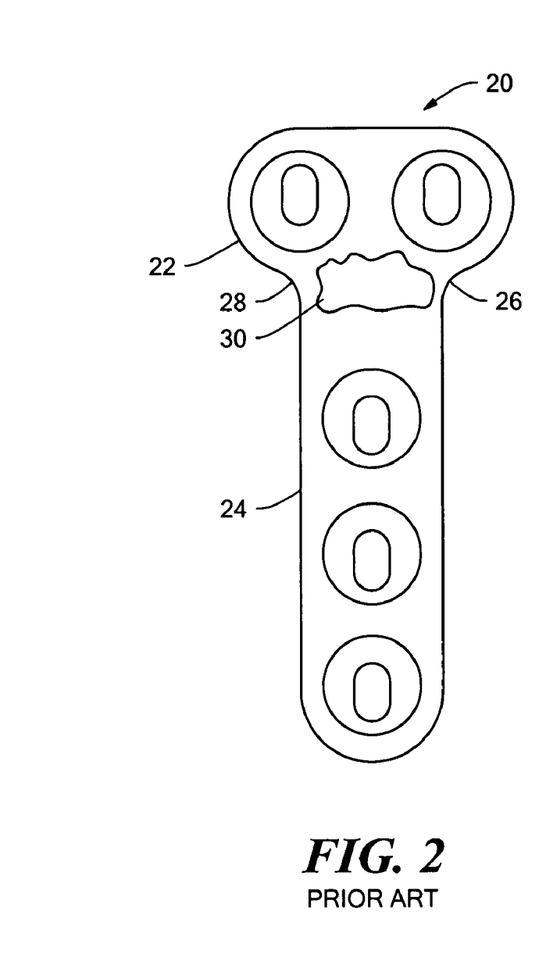
FIG. 2 is a front view of another bone fixation plate in accordance with the prior art.

The tibial osteotomy fixation plate 10, FIG. 1 of U.S. Pat. No. 5,304,180 is shown spanning curvilinear cut C wherein triangular portion 12 is to be attached to the metaphysis and leg portion 14 is to be attached to the tibia using bone screws (not shown) seated in apertures 16a-f. As discussed in the Background section above, plate 10 is cast from surgical grade stainless steel and thus is relatively thick (approximately 5 mm) and possibly toxic. Also, the somewhat sharp transition at area 18 between triangular portion 12 and leg 14 results in a weak area in region 19. T-shaped fixation plate 20, FIG. 2 includes base section 22 and leg section 24. The transition at areas 26 and 28 of this prior art fixation plate can also result in a weak area in region 30.

Figure 3:
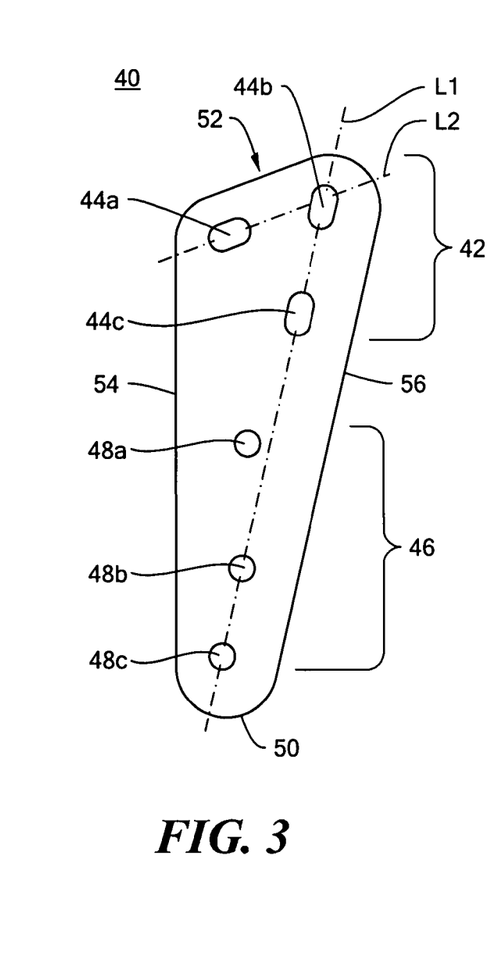
FIG. 3 is a schematic top view of one example of a bone fixation plate in accordance with the subject invention.

One example of a fixation plate 40, FIG. 3 in accordance with this invention, includes base section 42 including apertures 44a, 44b, and 44c for fixation to one bone segment (e.g., the medial segment), and leg section 46 including apertures 48a, 48b, and 48c for fixation to another bone segment (e.g., distal segment (diaphysis)).

The expanse of base section 42 preferably tapers gradually to smoothly co-join with leg section 46 which continues to smoothly taper to distal rounded end 50. The proximal end 52 of base section 42 is preferably angled away from the leg section as shown. Typically, both sides 54 and 56 of plate 40 are straight and side 56 smoothly diverges, from distal end 50 to proximal end 52, away from side 54. In this way, there are no sharp transitions reducing any weak areas in fixation plate 40 subject to failure.

Figure 4:
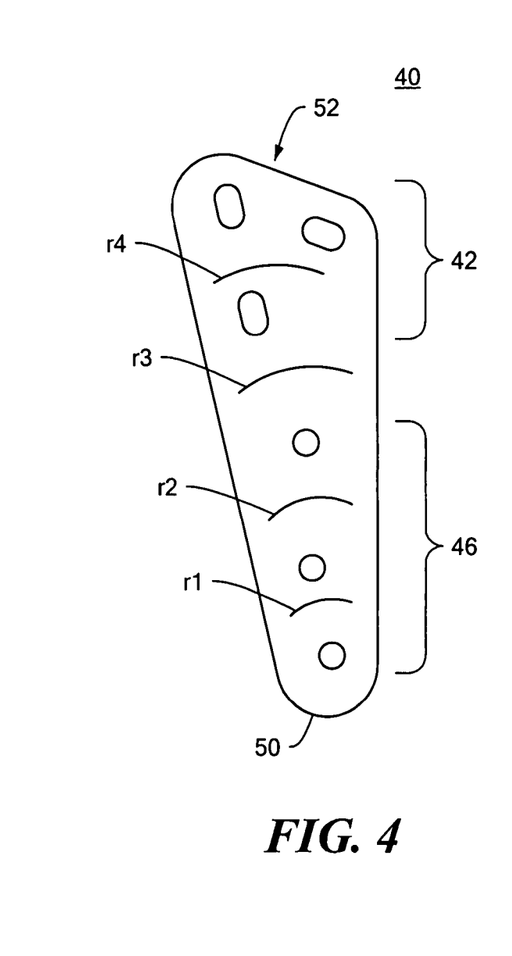
FIG. 4 is a schematic bottom view of the bone fixation plate shown in FIG. 3.
Figure 5:
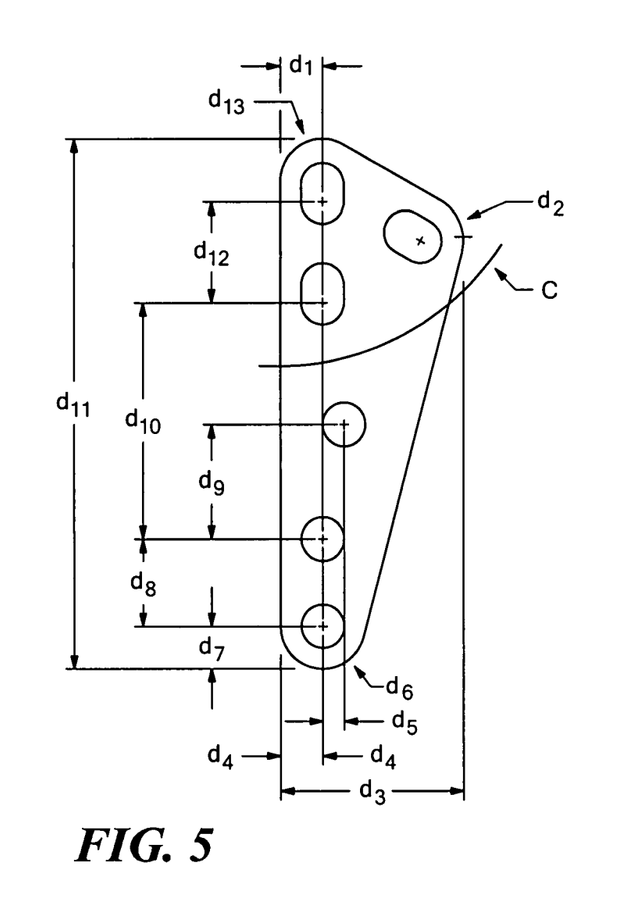
FIG. 5 is a another schematic top view of a bone fixation plate in accordance with the subject invention.
Figure 6:
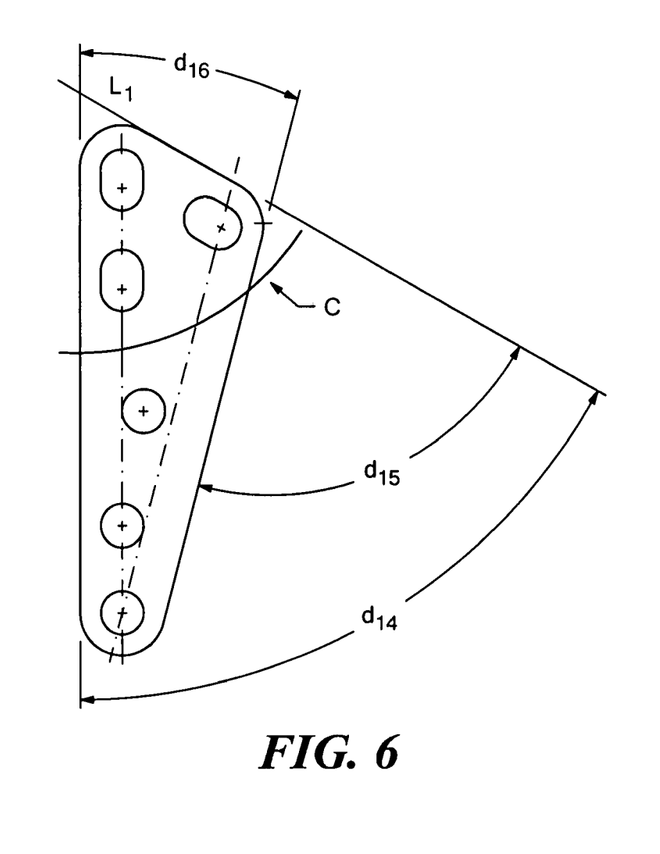
FIG. 6 is another view of the bone fixation plate shown in FIG. 5.
Figure 7:
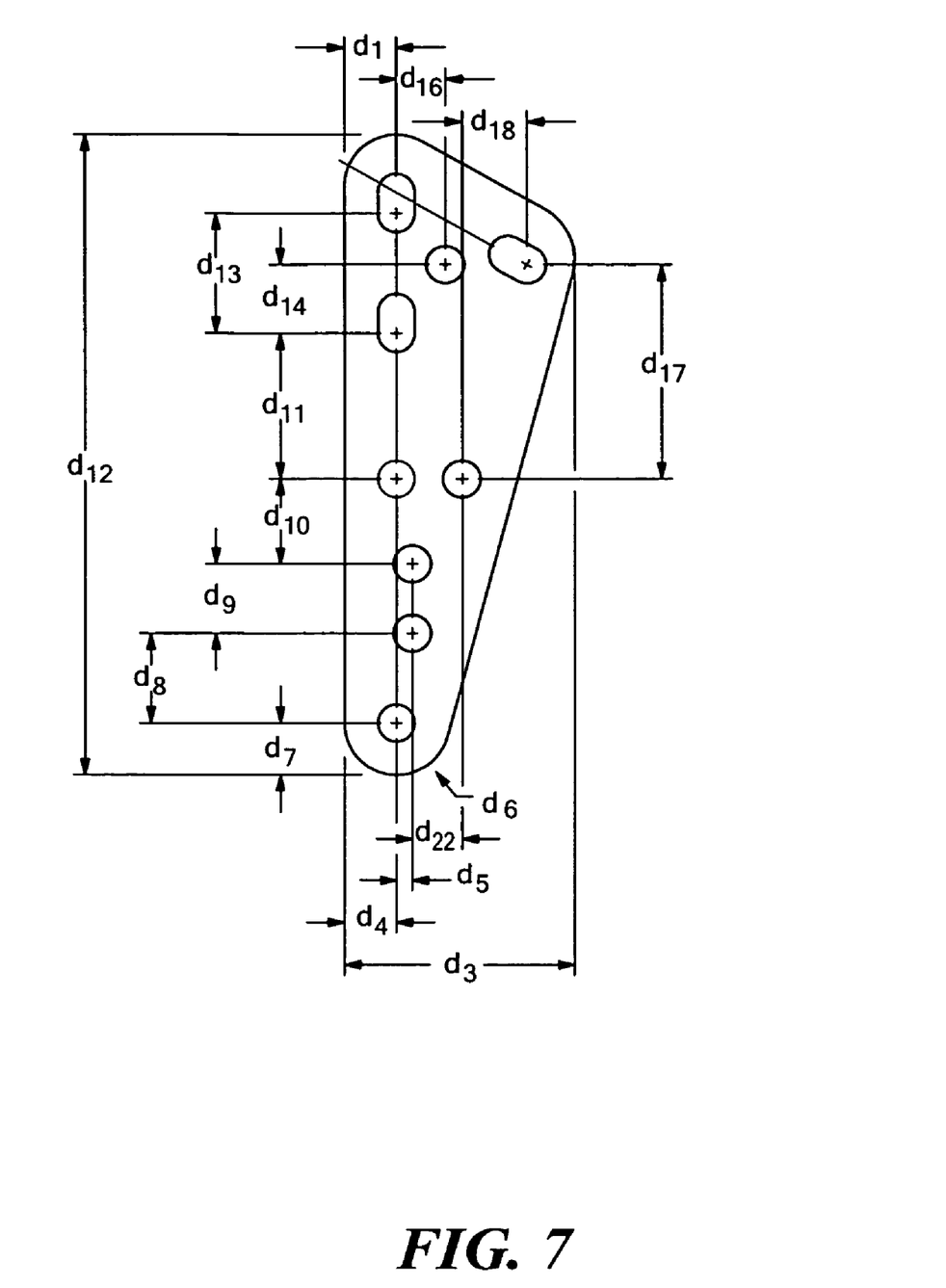
FIGS. 7-8 are schematic views of another example of a bone fixation plate in accordance with the subject invention.
Figure 8:
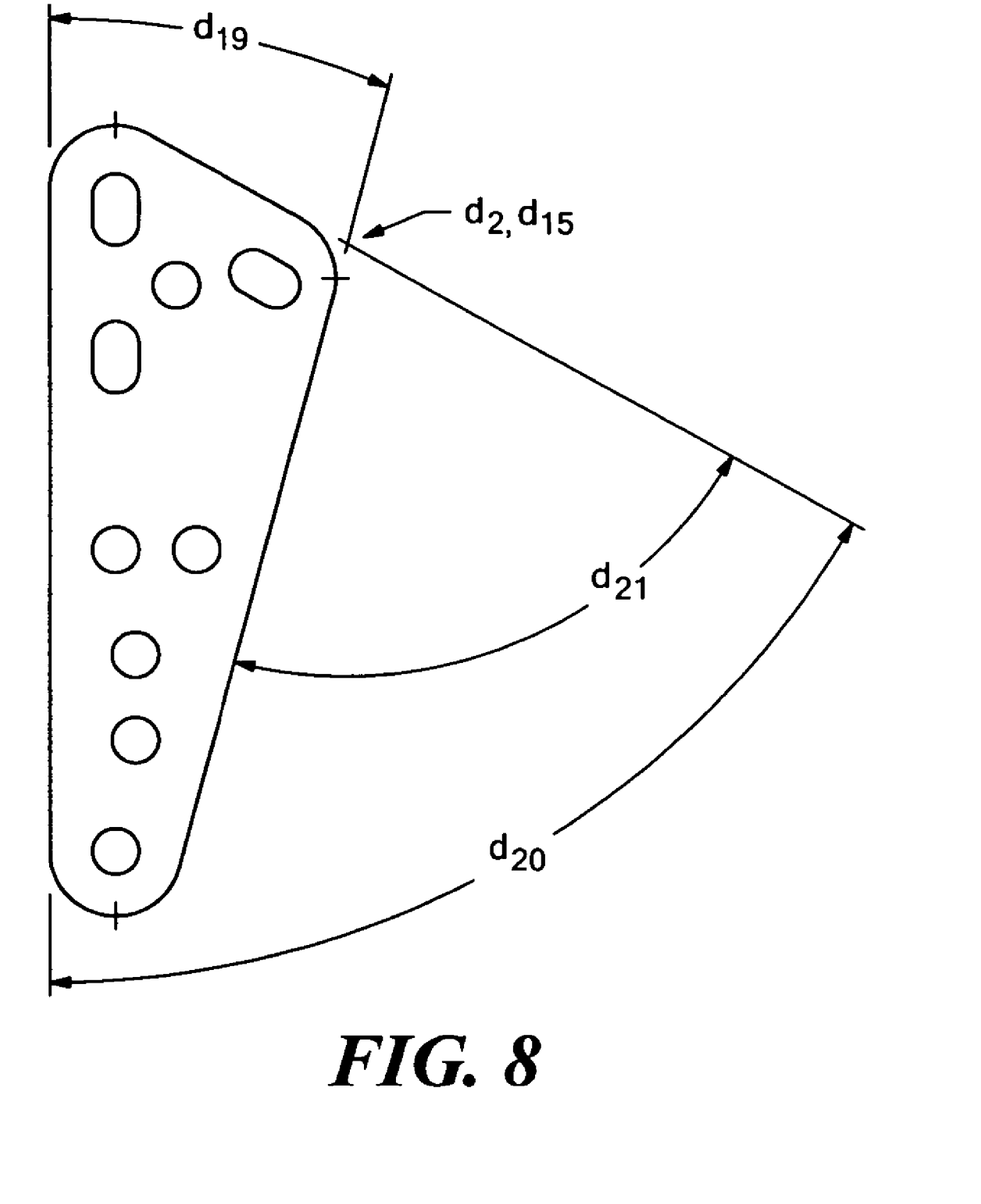

In the preferred embodiment, plate 40 is anatomically pre-contoured as shown in FIG. 4 and differently anatomically pre-contoured along the length thereof such that the curvature arc of base section 42 is generally greater than the curvature arc of leg section 46 and the change in contour from distal end 50 to proximal end 52 is smoothly progressive. Plate 40 is anatomically pre-contoured to closely fit the bone surface to which it is applied to reduce the amount of bending prior to fixation. In one example, the curvature arc at $r_1$, was 1.625, at $r_2$ was 1.219, at $r_3$ was 0.813, and at $r_4$ was 0.406.

Also in the preferred embodiment, the long axes of spaced elongate apertures 44b and 44c in base section 42, FIG. 3 lie on the same axis $L^1$ and the centers of spaced round apertures 48b and 48c in leg section 46 also lie on axis $L_1$. Third spaced elongate aperture 44b in base section 42 has a second long axis $L_2$ intersecting axis $L_1$ at an angle of between 55 and 60°. Third spaced round aperture 48a is offset from axis $L_1$ and is located at the proximal end of leg section 46.

All the elongate apertures in base section 42 preferably have at least one beveled end denoted as b in FIG. 3 and also beveled sides. Round apertures 48a-c in leg section 46 are beveled evenly around their circumferences. For strength, the minimum spacing between any two adjacent apertures in base section 42 is greater than 0.2". And, the minimum spacing between any two apertures in leg section 46 is greater than 0.2".

The preferred plate is machined out of surgical implant grade 316L stainless steel and has a thickness of between 0.175 and 0.275".

The dimensions in Table 1 below relate to examples of different size plates in accordance with the subject invention as shown in FIGS. 5-8. All values are in inches.

TABLE 1

| Dimension | Plate Example A (FIGS. 7-8) Value | Plate Example B (FIGS. 5-6) Value | Plate Example C (FIGS. 5-6) Value |
|---|---|---|---|
| $d_1$ | .250 ± .010 | .200 ± .010 | .15 ± .010 |
| $d_2$ | R.250 ± .010 | R.200 ± .010 | .15 ± .010 |
| $d_3$ | 1.050 ± .010 | .841 ± .010 | .631 ± .010 |
| $d_4$ | .250 ± .010 | .200 ± .010 | .15 ± .010 |
| $d_5$ | .066 ± .010 | .090 ± .010 | .070 ± .010 |
| $d_6$ | R.250 ± .010 | R.200 ± .010 | .15 ± .010 |
| $d_7$ | .250 ± .010 | .200 ± .010 | .15 ± .010 |
| $d_8$ | .408 ± .010 | .390 ± .010 | .293 ± .010 |
| $d_9$ | .325 ± .010 | .520 ± .010 | .390 ± .010 |
| $d_{10}$ | .405 ± .010 | 1.080 ± .010 | .811 ± .010 |
| $d_{11}$ | .700 ± .010 | 2.4 ± .010 | 1.5 ± .010 |
| $d_{12}$ | 3.0 ± .010 | .450 ± .010 | .340 ± .010 |
| $d_{13}$ | .563 ± .010 | R.200 ± .010 | .15 ± .010 |
| $d_{14}$ | .322 ± .010 | 60.000° ± .050° | 60.000° ± .050° |
| $d_{15}$ | R.250 ± .010 | 74.183° ± .050° | 74.183° ± .050° |
| $d_{16}$ | .207 ± .010 | 14.183° ± .050° | 14.183° ± .050° |
| $d_{17}$ | 1.007 ± .010 | | |
| $d_{18}$ | .303 ± .010 | | |
| $d_{19}$ | 14.145° ± .050° | | |
| $d_{20}$ | 60.00° ± .050° | | |
| $d_{21}$ | 74.145° ± .050° | | |
| $d_{22}$ | .215 ± .010 | | |

The result is an improved bone fixation plate useful in tibial osteotomy and other procedures. The fixation plate of this invention is thinner, lightweight, and strong and there are no sharp transitions between the two sections of the fixation plate.

Although specific features of the invention are shown in some drawings and not in others, however, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A fixation plate comprising:
   first, second, and third straight sides, the first straight side having a length less than one half the length of each of the second and third straight sides;
   the first straight side defining a proximal end;
   a distal end defined by an intersection of the second and third straight sides;
   the second straight side extending from the proximal end to the distal end;
   the third straight side spaced from the second side, longer than the second straight side, and extending from the proximal end to the distal end;

the second and third straight sides continuously diverging away from each other from the distal end to the proximal end defining a) a base section configured for fixation to one bone segment, the base section proximate the proximal end and b) a leg section configured for fixation to another bone segment, the leg section extending from the base section to the distal end;

a first long axis extending from the proximal end to the distal end;

at least two spaced elongated apertures, elongated along said first long axis, in the base section, and sharing the first long axis; and two spaced round apertures in the leg section having centers lying on said first long axis.

2. A fixation plate comprising:

first, second, and third straight sides, the first straight side having a length less than one half the length of each of the second and third straight sides;

the first straight side defining a proximal end;

a distal end defined by an intersection of the second and third straight sides;

the second straight side extending from the proximal end to the distal end;

the third straight side spaced from the second side, longer than the second straight side, and extending from the proximal end to the distal end;

the second and third straight sides continuously diverging away from each other from the distal end to the proximal end defining a) a base section configured for fixation to one bone segment, the base section proximate the proximal end and b) a leg section configured for fixation to another bone segment, the leg section extending from the base section to the distal end;

a first long axis extending from the proximal end to the distal end;

at least two spaced elongated apertures, elongated along said first long axis, in the base section, and sharing the first long axis;

two spaced round apertures in the leg section lying on said first long axis; and a third spaced aperture in the leg section offset from the first long axis.

3. A fixation plate comprising:

first, second, and third straight sides, the first straight side having a length less than one half the length of each of the second and third straight sides;

the first straight side defining a proximal end;

a distal end defined by an intersection of the second and third straight sides;

the second straight side extending from the proximal end to the distal end;

the third straight side spaced from the second side, longer than the second straight side, and extending from the proximal end to the distal end;

the second and third straight sides continuously diverging away from each other from the distal end to the proximal end defining a) a base section configured for fixation to one bone segment, the base section proximate the proximal end and b) a leg section configured for fixation to another bone segment, the leg section extending from the base section to the distal end;

a first long axis extending from the proximal end to the distal end;

two spaced elongated apertures, elongated along said first long axis, in the base section, sharing the first long axis, and having at least one beveled end and beveled sides; and at least one aperture in the leg section lying on said first long axis.

4. A fixation plate comprising:

first, second, and third straight sides, the first straight side having a length less than one half the length of each of the second and third straight sides;

the first straight side defining a proximal end;

a distal end defined by an intersection of the second and third straight sides;

the second straight side extending from the proximal end to the distal end;

the third straight side spaced from the second side, longer than the second straight side, and extending from the proximal end to the distal end;

the second and third straight sides continuously diverging away from each other from the distal end to the proximal end defining a) a base section configured for fixation to one bone segment, the base section proximate the proximal end and b) a leg section configured for fixation to another bone segment, the leg section extending from the base section to the distal end;

a first long axis extending from the proximal end to the distal end;

at least two spaced elongated apertures, elongated along said first long axis, in the base section, and sharing the first long axis; and spaced round beveled apertures in the leg section, at least one said aperture in the leg section lying on said first long axis.

5. A fixation plate comprising:

first, second, and third straight sides, the first straight side having a length less than one half the length of each of the second and third straight sides;

the first straight side defining a proximal end;

a distal end defined by an intersection of the second and third straight sides;

the second straight side extending from the proximal end to the distal end;

the third straight side spaced from the second side, longer than the second straight side, and extending from the proximal end to the distal end;

the second and third straight sides continuously diverging away from each other from the distal end to the proximal end defining a) a base section configured for fixation to one bone segment, the base section proximate the proximal end and b) a leg section configured for fixation to another bone segment, the leg section extending from the base section to the distal end;

a first long axis extending from the proximal end to the distal end;

at least two spaced apertures, elongated along said first long axis, in the base section, and sharing the first long axis; and at least two spaced apertures in the leg section having also sharing said first long axis.

6. A fixation plate comprising:

first, second, and third straight sides, the first straight side having a length less than one half the length of each of the second and third straight sides;

the first straight side defining a proximal end;

a distal end defined by an intersection of the second and third straight sides;

the second straight side extending from the proximal end to the distal end;

the third straight side spaced from the second side, longer than the second straight side, and extending from the proximal end to the distal end;

the second and third straight sides continuously diverging away from each other from the distal end to the proximal end defining a) a base section configured for fixation to one bone segment, the base section proximate the proximal end and b) a leg section configured for fixation to another bone segment, the leg section extending from the base section to the distal end;

a first long axis extending from the proximal end to the distal end;

at least two spaced apertures, elongated along said first long axis, in the base section, and sharing the first long axis;

at least two spaced apertures in the leg section sharing said first long axis; and a third spaced aperture in the leg section offset from the first long axis.

7. A fixation plate comprising:

first, second, and third straight sides, the first straight side having a length less than one half the length of each of the second and third straight sides;

the first straight side defining a proximal end;

a distal end defined by an intersection of the second and third straight sides;

the second straight side extending from the proximal end to the distal end;

the third straight side spaced from the second side, longer than the second straight side, and extending from the proximal end to the distal end;

the second and third straight sides continuously diverging away from each other from the distal end to the proximal end defining a) a base section configured for fixation to one bone segment, the base section proximate the proximal end and b) a leg section configured for fixation to another bone segment, the leg section extending from the base section to the distal end;

a first long axis extending from the proximal end to the distal end;

at least one elongated aperture, elongated along said first long axis, in the base section, and lying on the first long axis; and at least one aperture in the leg section lying on said first long axis.

8. A fixation plate comprising:

first, second, and third straight sides, the first straight side having a length less than one half the length of each of the second and third straight sides;

the first straight side defining a proximal end;

a distal end defined by an intersection of the second and third straight sides;

the second straight side extending from the proximal end to the distal end;

the third straight side spaced from the second side, longer than the second straight side, and extending from the proximal end to the distal end;

the second and third straight sides continuously diverging away from each other from the distal end to the proximal end defining a) a base section configured for fixation to one bone segment, the base section proximate to proximal end and b) a leg section configured for fixation to another bone segment, the leg section extending from the base section to the distal end;

a first long axis extending from the proximal end to the distal end;

at least one elongated aperture, elongated along said first long axis, in the base section, and lying on the first long axis; and spaced apertures in the leg section, at least one said aperture in the leg section lying on said first long axis.

9. A fixation plate comprising:

first, second, and third straight sides, the first straight side having a length less than one half the length of each of the second and third straight sides;

the first straight side defining a proximal end;

a distal end defined by an intersection of the second and third straight sides;

the second straight side extending from the proximal end to the distal end;

the third straight side spaced from the second side, longer than the second straight side, and extending from the proximal end to the distal end;

the second and third straight sides continuously diverging away from each other from the distal end to the proximal end defining a) a base section configured for fixation to one bone segment, the base section proximate the proximal end and b) a leg section configured for fixation to another bone segment, the leg section extending from the base section to the distal end;

a first long axis extending from the proximal end to the distal end;

at least two spaced elongated apertures, elongated along said first long axis, in the base section, and sharing the first long axis; and apertures in the leg section.

* * * * *